United States Patent [19]

Fannin

[11] 4,170,603
[45] Oct. 9, 1979

[54] NOVEL SUBSTITUTED METHYLENE BRIDGED ALUMINUM OLIGOMERS

[75] Inventor: Loyd W. Fannin, Dickinson, Tex.

[73] Assignee: Stauffer Chemical Company, Westport, Conn.

[21] Appl. No.: 774,005

[22] Filed: Mar. 3, 1977

[51] Int. Cl.² ............................................. C07F 5/06
[52] U.S. Cl. ........................ 260/448 A; 252/429 K; 252/431 K; 585/507; 585/511
[58] Field of Search ................................... 260/448 A

[56] References Cited

U.S. PATENT DOCUMENTS

| 3,509,189 | 4/1970 | Ort et al. | 260/448 A |
| 3,509,190 | 4/1970 | Ort et al. | 260/448 A |
| 3,577,450 | 5/1971 | Ort et al. | 260/448 A |
| 3,700,710 | 10/1972 | Mottus et al. | 260/448 A |
| 3,910,979 | 10/1975 | Eidt | 260/448 A |

*Primary Examiner*—Helen M. S. Sneed

*Attorney, Agent, or Firm*—Joel G. Ackerman

[57] ABSTRACT

Novel organoaluminum compounds having the formula

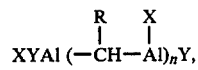

in which X is a halogen, Y is an alkyl group having from 1 to 10 carbon atoms, a phenyl group or a halogen, R is an alkyl group having from 2 to 9 carbon atoms, and n is an integer from 1 to 20. These compounds are less viscous and more soluble in hydrocarbon solvents than are corresponding ethylene-based or butadiene-based compounds.

The novel compounds are prepared by the reaction of alkylaluminum dihalides or aluminum trihalides with a terminal olefin having from 3 to 10 carbon atoms in the presence of aluminum metal.

19 Claims, No Drawings

NOVEL SUBSTITUTED METHYLENE BRIDGED ALUMINUM OLIGOMERS

BACKGROUND AND PRIOR ART

This application relates to novel aluminum compounds having the formula $$XYAl(-\underset{\underset{R}{|}}{C}H-\underset{\underset{X}{|}}{Al})_nY,$$

in which X is a halogen, Y is an alkyl group having from 1 to 10 carbon atoms, a phenyl group or a halogen, R is an alkyl group having from 2 to 9 carbon atoms, and n is an integer from 1 to 20.

U.S. Pat. No. 3,910,979 disclosed the preparation of compounds having the formula $$XYAl(Z-\underset{\underset{X}{|}}{Al})_nY,$$

in which X is a chlorine, bromine or iodine radical, Y is an alkyl or aryl radical, n is an integer from 1 to 20 and Z is an ethylene, 2-butenylene or alkyl substituted 2-butenylene group. These compounds are produced from ethylene, 1,3-butadiene or substituted 1,3-butadienes and are said to be suitable co-catalysts for polymerization of olefins.

The compounds produced from ethylene or butadienes form extremely viscous solutions with other aluminum alkyl or alkylaluminum halide compounds. They precipitate as solids when the viscous solutions are added to hydrocarbon solvents, and no solvents for the solids have been found except other aluminum alkyls. This high viscosity can present a manufacturing problem, especially in the filtration stage, and the low solubility limits their application.

A number of methylene-bridged aluminum compounds have also heretofore been synthesized, for example in U.S. Pat. Nos. 3,509,189; 3,509,190; 3,577,450; and 3,700,710. These are prepared from methylene chloride and aluminum metal, by various processes, as described in the patents.

SUMMARY OF THE INVENTION

This invention relates to novel organoaluminum compounds having the formula $$XYAl(-\underset{\underset{R}{|}}{C}H-\underset{\underset{X}{|}}{Al})_nY,$$

in which X is a halogen, Y is an alkyl group having from 1 to 10 carbon atoms, a phenyl group or a halogen, R is an alkyl group having from 2 to 9 carbon atoms, and n is an integer from 1 to 20.

This invention also relates to a process for preparing such compounds comprising reacting an aluminum compound selected from the group consisting of alkylaluminum dihalides, alkylaluminum sesqui-halides, aluminum trihalides, and precursors thereof with a terminal mono-olefin having from 3 to 10 carbon atoms, in the presence of metallic aluminum.

The novel organoaluminum compounds of the present invention are suitable as organoaluminum components or co-catalysts in two, three or other multi-component Ziegler catalysts for the polymerization of mono- or di-olefins.

DETAILED DESCRIPTION OF THE INVENTION

This application relates to novel organoaluminum compounds having the formula $$XYAl(-\underset{\underset{R}{|}}{C}H-\underset{\underset{X}{|}}{Al})_nY.$$

Y is an alkyl group having from 1 to 10 carbon atoms, a phenyl group, or a halogen radical. For example, Y may be an alkyl group such as methyl, ethyl, propyl, isopropyl, n-butyl, isobutyl, sec-butyl, tert.-butyl, pentyl, hexyl, heptyl, octyl, nonyl, decyl, or the like. Preferably Y is methyl or ethyl. Y may alternatively be a halogen, such as chlorine, bromine or iodine, or may be a phenyl group. X is a halogen, for example, chlorine, bromine or iodine. R is an alkyl group having from 2 to 9 carbon atoms, and may be a straight chain or branched chain alkyl group. For example, R may be ethyl, n-propyl, n-butyl, isobutyl, pentyl, hexyl, heptyl, octyl, nonyl and the like. n is an integer from 1 to 20, preferably from 1 to 10.

The new compounds, having the group $$-\underset{\underset{R}{|}}{C}H-$$

are thus of the alkylidene dialuminum type, i.e., the group $$-\underset{\underset{R}{|}}{C}H-$$

is propylidene, butylidene, pentylidene, etc., according to the length and character of R.

The new compounds of this invention, as depicted by the above formula, exist as an equilibrium mixture of two radical exchange forms of the types (I) and (II) below:

$$\underset{Y}{\overset{Y}{\diagdown}}Al[-\underset{\underset{R}{|}}{C}H-\underset{\underset{X}{|}}{Al}]_n-X \quad \underset{X}{\overset{Y}{\diagdown}}Al[-\underset{\underset{R}{|}}{C}H-\underset{\underset{X}{|}}{Al}]_n-Y$$
$$\text{(I)} \quad\quad\quad \text{(II)}$$

In general, the compounds of the present invention are prepared by the reaction of an alkylaluminum dihalide or an aluminum trihalide with a terminal mono-olefin in the presence of metallic aluminum. The terminal mono-olefin has 3 to about 10 carbon atoms and may be, for instance, a straight chain olefin such as propylene, 1-butene, 1-pentene, 1-hexene, 1-heptene, and the like.

Branched chain olefins should be selected bearing in mind the tendency of certain such olefins, particularly isobutylene, to polymerize even at room temperatures in the presence of aluminum trihalides and those alkylaluminum dihalides, such as methylaluminum dichloride and methylaluminum sesquichloride, which are Lewis acids. Preferred branched chain olefins for use in this invention are those having a primary chain of at least 5 carbon atoms in length; these do not readily polymerize in the presence of aluminum trihalides or alkylaluminum dihalides under the conditions employed. Thus, the preferred branched chain olefins may be for example, 2-methyl-1-pentene, 2-methyl-1-hexene, 2-ethyl-1-hexene, other methylpentenes, methylhexenes and ethylhexenes, and various ethylpentenes, dimethylpentenes, diethylpentenes, branched chain heptenes, octenes and the like. Isobutylene, however, can be employed in this invention, in combination with any alkylaluminum dihalide which does not tend to cause it to polymerize.

Thus, when X and Y are both halogen (the aluminum compound is an aluminum trihalide) or when Y is methyl (from methylaluminum dihalides or sesquihalides, i.e., Lewis acids), R is either a straight chain alkyl radical having from 2 to 9 carbon atoms or a branched chain alkyl radical having from 4 to 9 carbon atoms in the primary chain.

Of all the olefins useful in this invention, propylene is most preferred.

The aluminum utilized in the reaction is in the metallic form and may be in the form of shavings, foil, flakes, or powder. The aluminum does not require special chemical activators or milling; it is activated in situ in the presence of the alkylaluminum dihalide or aluminum trihalide.

In addition to alkylaluminum dihalides or aluminum trihalides there may be used as the starting materials, precursors thereof. These include sesquihalide compounds, which are equimolar mixtures of alkylaluminum mono-halides and dihalides. Additionally, the reactive dihalide species can be formed in situ by introducing precursors of the sesquihalides. For example, ethyl chloride and aluminum will react to give ethyl aluminum sesquichloride; therefore, ethyl chloride may be introduced as a reactant to the process. Similarly, trimethylaluminum will react with aluminum chloride to form methylaluminum dichloride; therefore, a mixture of trimethylaluminum and aluminum chloride may be used as starting materials. The trialkylaluminum or aluminum dihalide or precursor thereof may be in a solution or in a suspension of an inert solvent, or may be introduced as neat material.

In a preferred embodiment, powdered aluminum is slurried with the alkylaluminum dihalide, aluminum trihalide or precursor thereof, and is brought to reaction temperature. The particular olefin to be utilized is introduced into the reactor either beneath the liquid surface or into the vapor space above it at a pressure sufficient to keep a substantial portion of the olefin dissolved in the aluminum halide reactant mixture. The temperature will be as low as practical to permit reasonable rates and to prevent undesired side reactions and is preferably in the range of 50° C. to 150° C. The pressure utilized will vary according to the olefin introduced, but in general is as low as possible to prevent side reactions such as the so-called "growth reaction". Preferably, the pressure is in the range of 1 to 10 atmospheres, although higher pressures could be used with the higher molecular weight olefins which do not undergo the "growth reaction" as readily as the lower molecular weight olefins. The reaction is continued with stirring until olefin consumption ceases or the desired oligomer composition is obtained. In the case of gaseous and lowboiling olefins the reaction rate is conveniently monitored by observing the pressure drop. The progress of the reaction can also be followed by conventional analytical determination of the halide/aluminum ratio. As more aluminum is incorporated into the oligomer, the halide/aluminum ratio decreases until it approaches 1.

Since the oligomeric product does not become highly viscous, it can easily be separated from the unreacted aluminum by filtration or decantation. This is in contrast to the products produced from ethylene or butadienes which are highly viscous and cannot be readily separated in such a manner. It has also been found that the compounds of the present invention are much more soluble in hydrocarbon solvents than the corresponding compounds based on ethylene or butadiene.

The following examples are presented as illustrative of the invention but are not intended to limit the scope thereof in any way.

EXAMPLE 1

The apparatus used in the experiments was a heavy-walled 12-oz. borosilicate bottle fitted with an adjustable diptube. which permitted gas entry into the vapor space or beneath the surface of the liquid. The head assembly also included a pressure gauge and a pressure relief valve. The bottle was charged with 40 g. (1.43 g-atoms) of powdered aluminum (30–325 mesh) and 230 g. (2.04 moles) of methylaluminum dichloride under an atmosphere of dry nitrogen. The bottle was capped and placed in an oil bath at 100° C. for 30 minutes prior to adding the olefin. After the dichloride melted the slurry was stirred with a magnetic stirring bar. Propylene was fed on demand into the vapor spaced of the reactor at 30 psig. Periodically, the reactor was blocked in to permit observation of the pressure drop rate. The reaction was terminated after five hours, although propylene was still being consumed. The reaction consumed 37.7 g. (0.90 mole) of propylene, and a significant liquid volume increase was noted. The product was a transparent red solution and was quite fluid above its melting point, whereas product from a similar reaction using ethylene would have been too viscous to stir with a magnet. The product (m.p. 45–50° C.) solidified on cooling because of unreacted methylaluminum dichloride (m.p. 72° C.). A sample of the melted product solution was transferred by syringe to an evacuated vial capped with a rubber septum. After centrifuging, a portion of the sample was submitted for elemental and gas anaylses, and another portion was sealed in a tube for proton magnetic resonance (pmr) spectroscopic analysis. Analysis of the hydrolysis gas by gas chromatography gave the following:

| Component | Normalized Mole % |
| --- | --- |
| Methane | 84.03 |
| Ethane | 0.33 |
| Propane | 12.78 |
| Isobutane | 2.81 |
| Hydrogen | 0.06 |

Titration analyses gave 21.18% Al and 51.75% Cl for a Cl/Al atomic ratio of 1.86. Intepretation of the pmr spectrum indicated a 1,1-dialuminum propane structure for the product.

EXAMPLE 2

The reactor described in Example 1 was charged with 40 g. (1.48 g. -atoms) of powdered aluminum and 116 g. (0.91 mole) of ethylaluminum dichloride. After heating the reactor contents to 95° C., propylene was fed on demand at 30–40 psig. The temperature was increased to 105° C. after about 24 hours to increase the reaction rate. A total of 60.7 g. (1.45 mole) of propylene was consumed after 34 hours total reaction time, at which point the reaction was terminated. The final crude product was a very dark red-brown liquid which was quite fluid even at room temperature. About 75% of the crude product was vacuum-distilled as a colorless liquid leaving a highly viscous pot residue. The following analyses were obtained from the crude product and distillate:

| Hydrolysis Gas (mole %) | Crude Product | Distillate |
| --- | --- | --- |
| Methane | 1.19 | 0.05 |
| Ethane | 54.19 | 61.27 |
| Propane | 41.39 | 38.21 |
| Propylene | 3.20 | 0.37 |
| Hydrogen | 0.04 | 0.10 |
| Aluminum, wt % | 18.65 | 19.63 |
| Chloride, wt % | 36.32 | 40.90 |
| Cl/Al atomic ratio | 1.48 | 1.58 |

EXAMPLE 3

The bottle reactor described in Example 1 was charged with 229 g. (2.03 moles) of laboratory prepared methylaluminum dichloride and 40 g. (1.48 g.-atoms) of powdered aluminum. The reaction was conducted as described in Example 1 except that 1-butene was fed to the reactor rather than propylene (at 22 psig). The reaction was terminated after three hours, although the olefin was still being consumed. The reaction consumed 46.0 g. (0.82 mole) of 1-butene, resulting in a red-orange, non-viscous solution which crystallized on cooling.

The product was found to contain 20.20% Al and 46.93% Cl, giving a Cl/Al ratio of 1.77. The hydrolysis gas contained 15 mole% n-butane.

EXAMPLE 4

The bottle reactor described in Example 1 was charged with 134 g. (0.54 mole) of ethylaluminum sesquichloride and 40 g. (1.48 g.-atoms) of powdered aluminum. 1-Hexene, which had been passed through a bed of activated alumina, was added dropwise to the reactor, which was maintained at room temperature. After the addition of 45 g. (0.53 mole) of 1-hexene, the resulting red-orange slurry was heated at 100° C. for seven hours. The vapor pressure, which was initially 30 psig at 100° C., decreased to 22 psig within the first hour and remained at that pressure during the remainder of the reaction.

Analyses of the final transparent, red product showed that the Cl/Al ratio had decreased to 1.46 from the initial ratio of 1.53 in the sesquichloride sample used. The hydrolysis product was found to contain n-hexane.

EXAMPLE 5

The bottle reactor described in Example 1 is charged with 40 g. (1.48 g.-atoms) of powdered aluminum and 100 g. (0.375 mole) of anhydrous aluminum tribromide. Methylcyclohexane (150 g.) is transferred into the bottle and the reactor is placed into an oil bath at 95° C. for 30 minutes prior to adding the olefin. Propylene is fed on demand into the vapor space at 30 psig. The reactor is stirred until propylene consumption ceases. Methylcyclohexane is chosen as solvent because of the high solubility of aluminum tribromide. A small amount of isomerization to dimethylcyclopentanes is experienced, but this does not adversely affect the preparation of the aluminum compound. The Br/Al ratio of the product is substantially lower than 3 depending on the amount of propylene added.

EXAMPLE 6

This Example was carried out to demonstrate the utility of these new compounds as polymerization co-catalysts. The distilled product from Example 2 was tested as a co-catalyst with titanium trichloride for the polymerization of propylene. Polymerization was carried out at 8 psia hydrogen initial charge, 140 psig total pressure, 70° C. temperature, and a ratio of aluminum:-titanium of 2. Run time was four hours. One hundred five grams of polymer, with an isotactic index of 61, was prepared per gram of TiCl$_3$. In a second experiment run under the same conditions, but with triethylaluminum added to adjust the Cl/Al ratio to 1.01, the catalyst's activity increased to 1170 g. of polymer per gram of TiCl$_3$, but the isotactic index decreased to 48.

I claim:

1. A compound having the formula

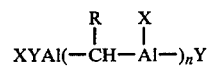

in which X is a halogen, Y is an alkyl group having from 1 to 10 carbon atoms, a phenyl group or a halogen, R is an alkyl group having from 2 to 9 carbon atoms, and n is an integer from 1 to 20, provided that wneh X and Y are both halogen or when Y is methyl, R is a straight chain alkyl group having from 2 to 9 carbon atoms or a branched chain alkyl radical having from 4 to 9 carbon atoms in the primary chain.

2. A compound according to claim 1 in which Y is methyl.

3. A compound according to claim 1 in which Y is ethyl.

4. A compound according to claim 1 in which Y is chloro.

5. A compound according to claim 1 in which X is chloro and Y is chloro.

6. A compound according to claim 1 in which R is ethyl.

7. A compound according to claim 1 in which R is n-propyl.

8. A compound according to claim 1 in which R is n-pentyl.

9. A compound according to claim 1 in which X is chloro.

10. A compound according to claim 1 in which X is bromo.

11. A process for the production of a compound having the formula

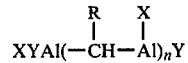

in which X is a halogen, Y is an alkyl group having from 1 to 10 carbon atoms, an aryl group or a halogen, R is an alkyl group having from 2 to 9 carbon atoms, and n is an integer from 1 to 20, comprising reacting an aluminum compound selected from the group consisting of alkylaluminum dihalides, alkylaluminum sesquihalides, aluminum trihalides and precursors thereof with a terminal mono-olefin having from 3 to 10 carbon atoms in the presence of metallic aluminum.

12. A process according to claim 11 in which the aluminum compound is an alkylaluminum dihalide.

13. A process according to claim 12 in which the aluminum compound is methylaluminum dichloride.

14. A process according to claim 12 in which the aluminum compound is ethylaluminum dichloride.

15. A process according to claim 11 in which the aluminum compound is prepared in situ by the reaction of an alkyl halide with metallic aluminum.

16. A process according to claim 11 in which the aluminum compound is an alkylaluminum sesquihalide.

17. A process according to claim 11 in which the aluminum compound is an aluminum trihalide.

18. A process according to claim 11 in which the olefin is propylene.

19. A process according to claim 11 in which the temperature is between about 50° C. and about 150° C.

* * * * *

UNITED STATES PATENT AND TRADEMARK OFFICE
CERTIFICATE OF CORRECTION

PATENT NO. : 4,170,603
DATED : October 9, 1979
INVENTOR(S) : Loyd W. Fannin

It is certified that error appears in the above-identified patent and that said Letters Patent are hereby corrected as shown below:

Change the Assignee from "Stauffer Chemical Company, Westport, Conn." to ---Texas Alkyls, Inc., Deer Park, Texas---.

Signed and Sealed this

Twenty-second Day of January 1980

[SEAL]

Attest:

SIDNEY A. DIAMOND

Attesting Officer

Commissioner of Patents and Trademarks